United States Patent [19]

Warriner

[11] Patent Number: Plant 5,638

[45] Date of Patent: Jan. 21, 1986

[54] ROSE PLANT JACAIM

[75] Inventor: William A. Warriner, Tustin, Calif.

[73] Assignee: Jackson & Perkins Company, Medford, Oreg.

[21] Appl. No.: 596,828

[22] Filed: Apr. 4, 1984

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Klarquist, Sparkman, Campbell, Leigh & Whinston

[57] ABSTRACT

A hybrid tea rose variety having a vigorous, upright plant, petals which change in color from near white to dark red as blooms open, and little or no fragrance.

1 Drawing Figure

This present invention relates to a new and distinct variety of rose plant of the hybrid tea class which was originated by me by crossing the variety Sunfire, U.S. Plant Pat. No. 3,510, with the variety Spellbinder, U.S. Plant Pat. No. 3,571.

The primary objective of this breeding was to produce a new rose variety combining the photosensitive pigment characteristic of Spellbinder with more floriferous characteristic of the variety Sunfire. This objective was substantially achieved along with other desirable improvements as evidenced by the following unique combination of characteristics which are outstanding in the new variety and which distinguish it from its parents, as well as from all other varieties of which I am aware:

1. A vigorous, upright, hybrid tea plant.
2. Photosensitive pigment in the petals, changing from near white to dark red as the blooms open.
3. Little or no fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Sunfire, U.S. Plant Pat. No. 3,510.

*Pollen parent.*—Spellbinder, U.S. Plant Pat. No. 3,571.

Classification:

*Botanical.*—Rosa hybrid.

*Commercial.*—Hybrid tea.

FLOWER

Observations made from specimens grown at Irvine, Calif. in November.

Blooming habit: Continuous.

Bud:

*Size.*—1" to $1\frac{1}{4}$" when petals start to unfurl.

*Form.*—Pointed ovoid.

*Color.*—When sepals first divide, Red Group 54C until changed upon exposure to sunlight to Red Group 53A, the basal area remaining lighter color Red 54C blended with yellow. When half blown, upper side of petals: outer rows of petals Red 53B where exposed; inner petals most recently unfolded. Center petals near Red Group 54C suffused with yellow pigments. When half blown, lower side of petals same as upper side in center of flower. Outer petals lighter on under sides.

*Sepals.*—Color: Green 138A. Surface texture: Numerous stipitate glands. Three appendaged sepals lightly appendaged. Two unappendaged sepals hairy edged.

*Receptacle.*—Color: Green 138A. Shape: Funnel. Size: Large, broad. Surface: Glandular.

*Peduncle.*—Length: Short. Surface: Glandular. Color: Light green. Strength: Stiff, erect.

*Opening.*—Spiral.

Bloom:

*Size.*—Medium. Average open size: 4".

*Borne.*—Singly.

*Stems.*—Medium, strong.

*Form.*—When first open, high centered. Permanence: Flattens, outer petal edges slightly curled.

*Petalage.*—Number of petals under normal conditions: approximately 40.

*Color.*—Center of flower: Upper side of petals, when very freshly opened, near Red Group 56C to D, lightly suffused with yellow; reverse side of petals — same; base of petals, Yellow Group 7A. Major color: Red 56C changing to Red 53A upon exposure to sunlight. Color remains near white (Red 56C) under overlapping petals. Outer petals darken first to Red 53A, giving a multicolor effect.

*Variegations.*—As described.

*Discoloration.*—General tonality at end of first day: See above description. Third day; Color continues to darken.

*Fragrance.*—None.

Petals:

*Texture.*—Thin.

*Shape.*—Round.

*Form.*—Edges slightly quilled.

*Arrangement.*—Imbricated. Petaloids in center: few.

*Persistence.*—Drop off cleanly.

*Lastingness.*—On the plant, long. As cut flower, long.

Reproductive parts:

*Anthers.*—Large, many. Color: Pale yellow. Arrangement: Regular around styles.

*Filaments.*—Color: Reddish.

*Styles.*—Color: Greenish white.

*Stigmas.*—Color: Greenish white.

PLANT

Form: Bush.

Growth: Vigorous, upright.

Foliage: Number of leaflets on normal mid-stem leaves: 5 and 7.

*Size.*—Medium.

*Quantity.*—Normal.

*Color.*—New foliage: Green suffused with Greyed Purple 183C. Old foliage: Dark green.

Leaflets:

*Shape.*—Oval.

*Texture.*—Leathery on upper side.

*Edge.*—Serrated.

*Serration.*—Single, small.

*Petiole.*—Rachis: Color: Green or reddish. Underside: Prickles.

*Stipules.*—Long, bearded.

*Disease resistance.*—Normally resistant to mildew under normal growing conditions at Irvine, Calif.

Wood:

*New wood.*—Color: Light green. Bark: Smooth.

*Old wood.*—Color: Dark green. Bark: Smooth.

Prickles:

*Quantity.*—On main canes from base: Few. On laterals from main canes: Few.

*Form.*—Long, straight.

*Color when young.*—Brown.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its vigorous, upright plant, photosensitive pigments aging from near white to dark red, and little to no fragrance.

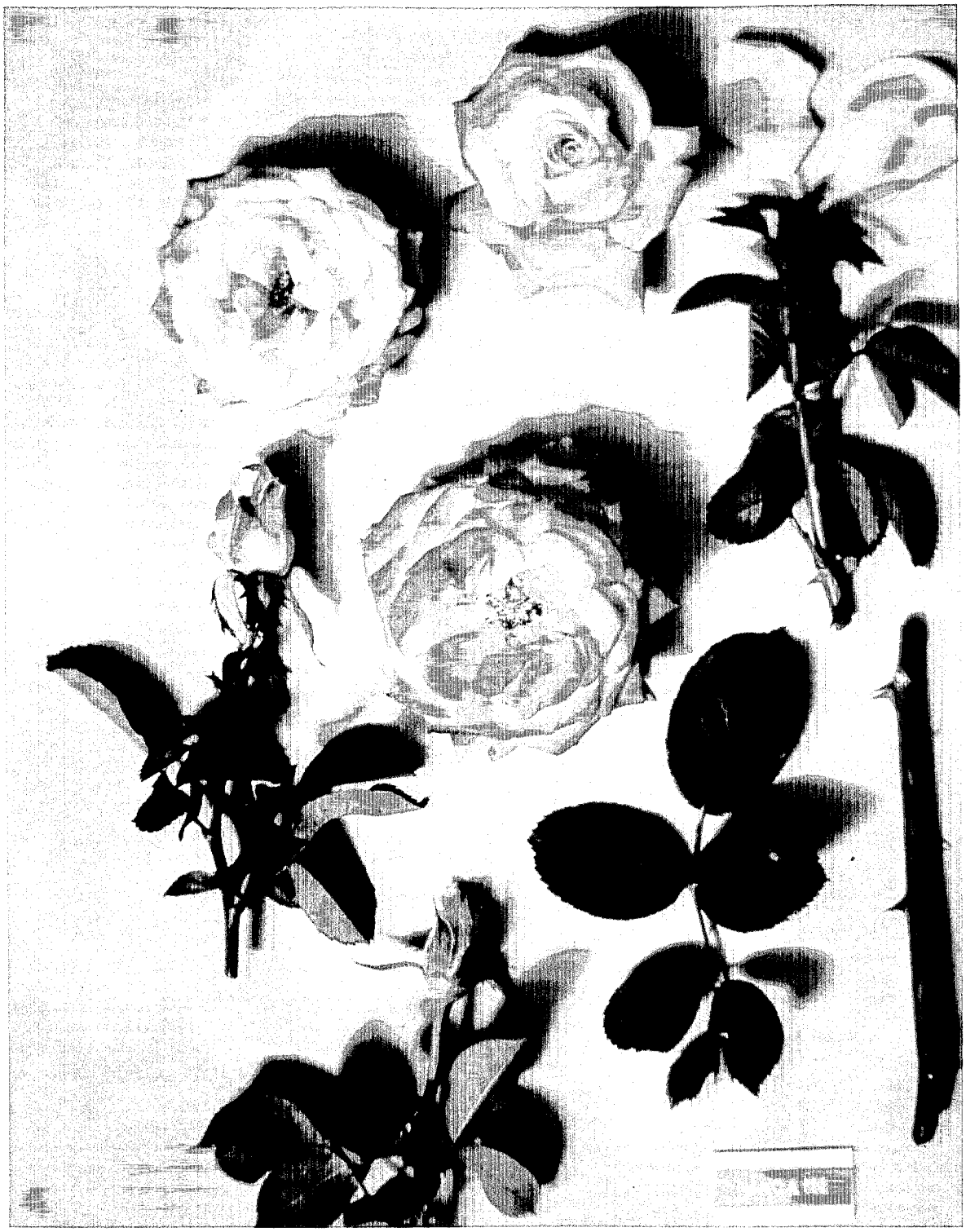

* * * * *